US012653726B2

(12) United States Patent

Gastaldo et al.

(10) Patent No.: US 12,653,726 B2
(45) Date of Patent: Jun. 16, 2026

(54) TRANSFER PAD WITH MOISTURE CONTROL

(71) Applicant: EHOB, Inc., Indianapolis, IN (US)

(72) Inventors: Christian Gastaldo, Indianapolis, IN (US); Gregory R. Konkle, Indianapolis, IN (US); Travis White, Fishers, IN (US)

(73) Assignee: EHOB, Inc., Indianpolis, IN (US)

( * ) Notice: Subject to any disclaimer, the term of this patent is extended or adjusted under 35 U.S.C. 154(b) by 650 days.

(21) Appl. No.: 18/059,750

(22) Filed: Nov. 29, 2022

(65) Prior Publication Data

US 2023/0248582 A1      Aug. 10, 2023

Related U.S. Application Data

(60) Provisional application No. 63/267,628, filed on Feb. 7, 2022.

(51) Int. Cl.
| | |
|---|---|
| *A61F 13/15* | (2006.01) |
| *A61F 13/51* | (2006.01) |
| *A61F 13/513* | (2006.01) |
| *A61F 13/53* | (2006.01) |
| *A61F 13/534* | (2006.01) |

(52) U.S. Cl.
CPC .................. *A61F 13/15756* (2013.01); *A61F 2013/15056* (2013.01); *A61F 2013/15308* (2013.01); *A61F 2013/51019* (2013.01); *A61F 2013/51316* (2013.01); *A61F 2013/530481* (2013.01); *A61F 2013/53472* (2013.01)

(58) Field of Classification Search
CPC . A61F 2013/15056; A61G 1/01; A61G 7/001; A61G 7/1025; A61G 7/1026
See application file for complete search history.

(56) References Cited

U.S. PATENT DOCUMENTS

| | | |
|---|---|---|
| 8,791,321 B2 | 7/2014 | Love et al. |
| 9,724,256 B2 | 8/2017 | Love et al. |
| 9,808,387 B2 | 11/2017 | Love et al. |

(Continued)

OTHER PUBLICATIONS

Wright, Lauren, How to Bind a Quilt, Nov. 18, 2020, Molly and Mama, www.mollyandmama.com.au/how-to-bind-a-quilt/ (Year: 2020).*

*Primary Examiner* — Jessica Arble
(74) *Attorney, Agent, or Firm* — Maginot, Moore & Beck LLP

(57) ABSTRACT

A transfer pad is provided for use in transferring a person reclining on a bed with bed linens that includes a top sheet formed from a fluid permeable material, a bottom sheet and an absorbent core contained within the top and bottom sheet. The bottom sheet has a bottom surface formed of a material having a coefficient of friction adapted to slide on the bed linens with the patient on the transfer pad. The top and bottom sheets are connected at a fluid leak-proof seam around a perimeter of the top and bottom sheets. The absorbent core is disposed within the perimeter and includes in sequence a first tissue sheet, a fluid absorbent sheet formed of a cellulosic pulp and a super-absorbent polymer (SAP) and a second tissue sheet. The absorbent pad includes handles along each side that can be grasped by a caregiver to slide the transfer pad, with a patient thereon, across the bed linens.

17 Claims, 5 Drawing Sheets

(56)                    References Cited

U.S. PATENT DOCUMENTS

| | | | |
|---|---|---|---|
| 2012/0005837 A1* | 1/2012 | Spahn | A61G 7/05784 |
| | | | 5/706 |
| 2012/0053545 A1* | 3/2012 | Love | B32B 7/14 |
| | | | 604/374 |
| 2012/0203152 A1* | 8/2012 | Thompson | A61F 5/01 |
| | | | 602/5 |
| 2018/0193213 A1* | 7/2018 | Spahn | B32B 5/26 |
| 2020/0281762 A1 | 9/2020 | Harvey et al. | |
| 2023/0061295 A1* | 3/2023 | Cowan | A61G 7/1021 |
| 2023/0110444 A1* | 4/2023 | Kurt | A61F 13/51394 |
| | | | 604/361 |

\* cited by examiner

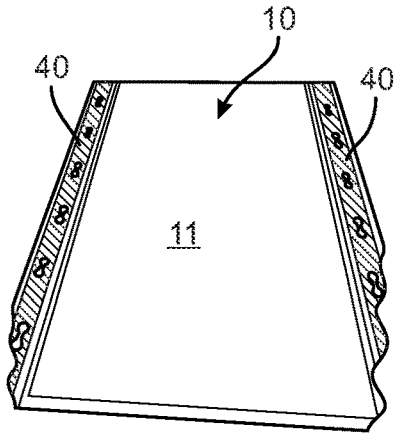

STEP 1: LAY PRODUCT FLAT WITH
ABSORBENT CORE UP

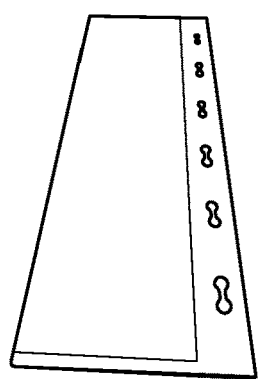

STEP 2: FOLD PRODUCT IN HALF
ALONG THE VERTICAL MIDLINE

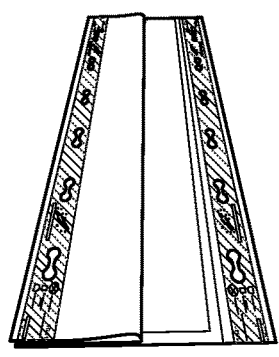

STEP 3: FOLD THE FACE UP SIDE BACK
OVER ITSELF SO THE GREEN HANDLE
IS FACING UP

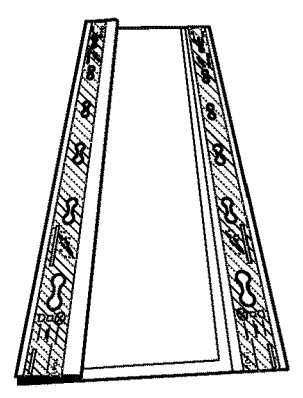

STEP 4: FOLD ABSORBENT CORE
UNDER THE EXPOSED HANDLE

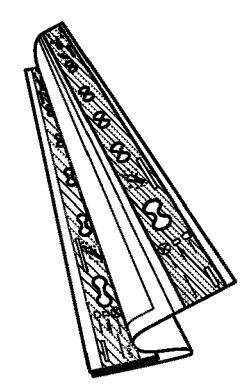

STEP 5: REPEAT ON OTHER SIDE LEAVING
GREEN HANDLE FACING UP

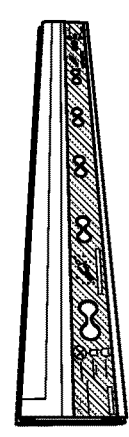

STEP 6: PRODUCT SHOULD
APPEAR LIKE THIS

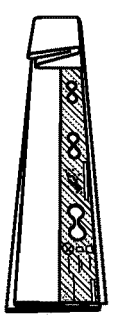

STEP 7: FOLD PRODUCT OVER ITSELF

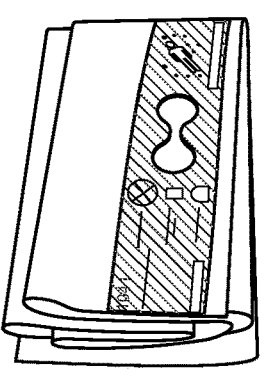

FINAL FOLDING APPEARANCE

FIG. 9

TRANSFER PAD WITH MOISTURE CONTROL

PRIORITY CLAIM

This application is a utility filing from and claims priority to U.S. Provisional Application No. 63/267,628, filed on Feb. 7, 2022, the entire disclosure of which is incorporated herein by reference.

BACKGROUND

Patients in a medical care facility often require movement from one location to another within the facility or movement within the patient's room to replace linens and tend to the patient. Bed-ridden patients or patients recovering from medical procedures are often not able to or permitted to move themselves, so patient transfers require nurse intervention. Safe patient handling is extremely important because moving patients throughout the day can be physically demanding and dangerous for nurses. Moving immobile patients is a significant contributing factor behind why nursing is one of the highest risk professions in terms of musculo-skeletal injuries.

In addition to safety, patient comfort is important, particularly for bed-ridden patients. Many such patients can be incontinent, so providing an absorbent pad is important to wick away the moisture and improve patient comfort. However, providing an absorbent pad comes at a cost to the caregiver or nursing staff. In particular, the pad must be removed and replaced when the patient's hospital gown and undergarments are replaced. It is thus necessary to not only obtain replacement garments and absorbent pad, but to also secure a transfer sheet to move the patient as needed. Many hospitals are understaffed so the time spent obtaining, positioning and removing multiple sheets and chux is a significant tax on the staff's time and efficiency.

There is a need for a transfer sheet or pad that combines moisture control with the ability to move a bed-ridden patient. The transfer pad must be strong enough to move a heavy patient and must be able to maintain that strength even when wet.

SUMMARY OF THE DISCLOSURE

A transfer pad is provided for use in transferring a person reclining on a bed with bed linens. The transfer pad includes a top sheet formed from a fluid permeable material, a bottom sheet and an absorbent core contained within the top and bottom sheet. The bottom sheet has a bottom surface formed of a material having a coefficient of friction adapted to slide on the bed linens with the patient on the transfer pad. The top sheet and the bottom sheet are substantially identically sized with a length sized so that the pad can extend from the thighs to the neck of the patient. The top and bottom sheets are connected at a fluid leak-proof seam around a first perimeter of the top and bottom sheets. The absorbent core is disposed within the first perimeter and includes in sequence a first tissue sheet, a fluid absorbent sheet formed of a cellulosic pulp and a super-absorbent polymer (SAP) and a second tissue sheet. The absorbent pad includes handles along each side that can be grasped by a caregiver to slide the transfer pad, with a patient thereon, across the bed linens. The transfer pad of the present disclosure is capable of moving a patient weighing 400 lbs. or more across a bed even when the absorbent core is soaked with body fluids.

DESCRIPTION OF THE DRAWINGS

FIG. 9 is a series of pictures showing the steps in folding the transfer pad of the present disclosure for compact packaging.

DETAILED DESCRIPTION

Figure 1:
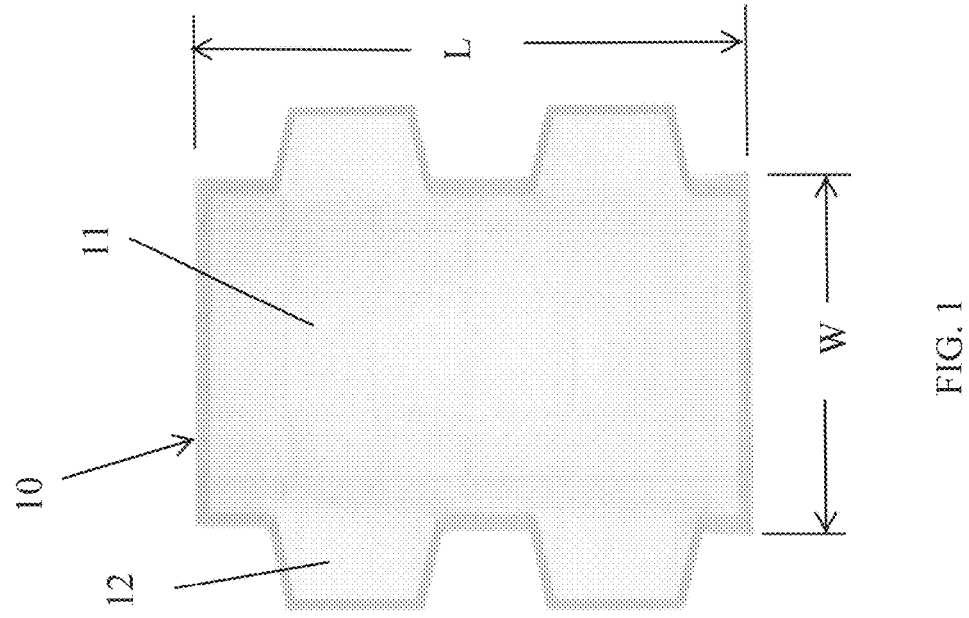
FIG. 1 is a top view of a transfer pad according to one embodiment of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
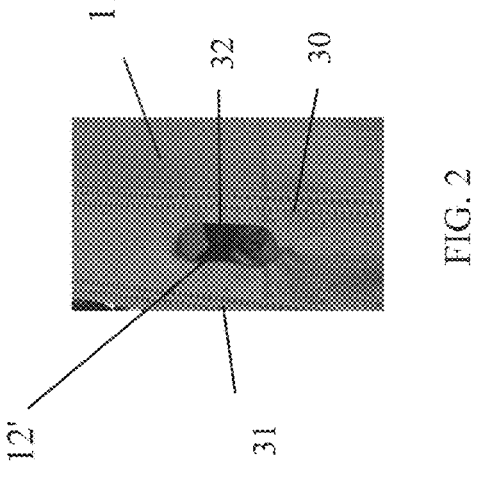
FIG. 2 is detail view of a handle portion of a transfer pad according to another embodiment of the present disclosure.
Figure 3:
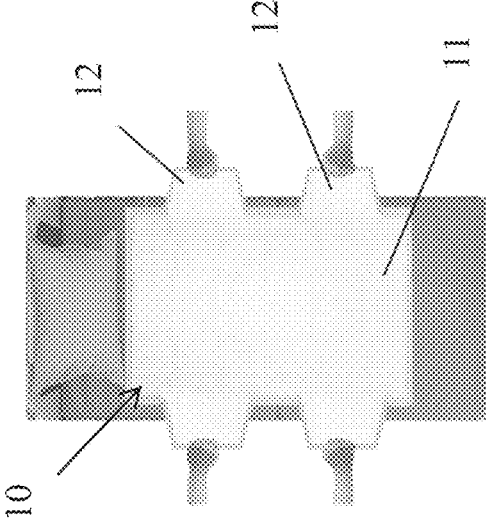
FIG. 3 is top view of the transfer pad of FIG. 1 being grasped in a use position of the pad.
Figure 5:
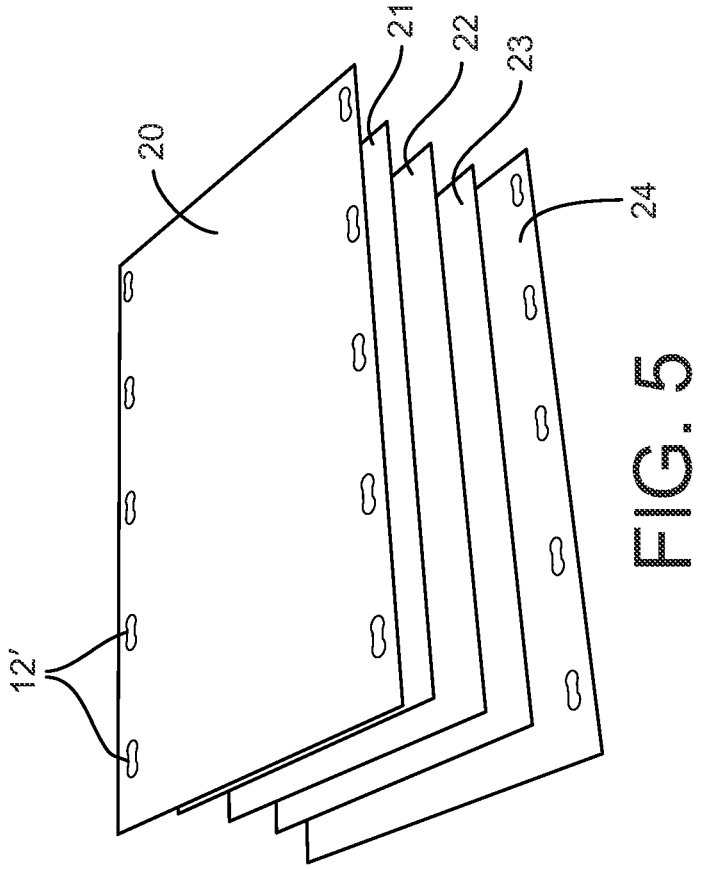
FIG. 5 is a perspective exploded view of the layers of the transfer pad of the present disclosure.

To address these concerns, a transfer pad 10 is provided with a body 11 designed for safety and comfort, as shown in FIG. 1. The transfer pad 10 includes at least a pair of handles 12 integrally formed with the body 11 on opposite sides of the transfer pad 10. The handles 12 can be protrusions from the side of the body as shown in FIG. 1, or can be cut-outs 12' as shown in FIGS. 2 and 5. It is also contemplated that the cut-outs 12' may be formed in the protrusions 12. As shown in FIG. 3, the handles 12 may be gripped by a caregiver or hospital staff on opposite sides of the transfer pad 10 to move the patient. The transfer pad has a length L and a width W that is sized to cover a substantial portion of, but not the entirety of, the bed. Preferably, the width W is slightly greater than the width of the bed, as shown in FIG. 3, to allow for easy access to the handles 12 or cut-outs 12'. The length L is preferably sufficient to receive the patient's torso and upper leg, and in one embodiment to extend from the neck to the knees of the patient. The length L is at least 39 inches, less than 72 inches, and preferably 56 inches. The width is between 30 inches and 45 inches. Preferably, the transfer pad can be provided in three distinct lengths—39, 56 and 72 inches—to accommodate different heights of patients.

Figure 4:
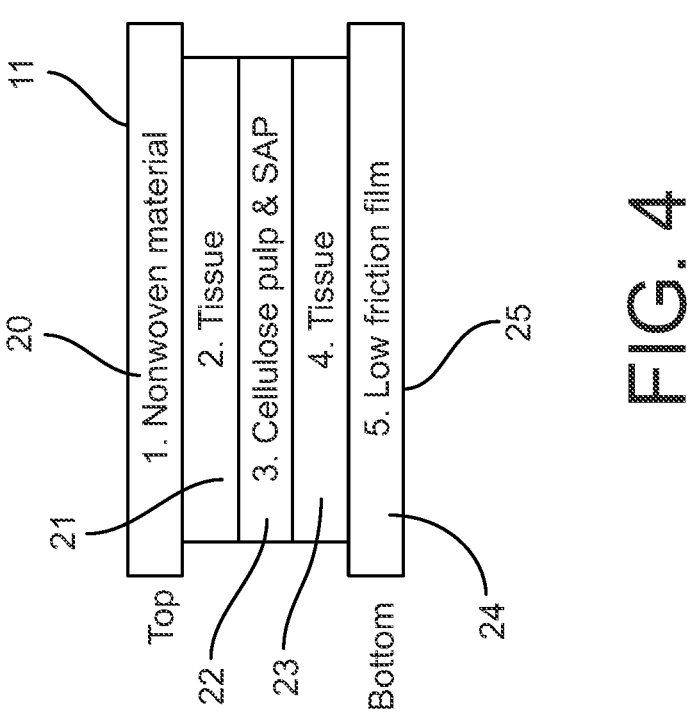
FIG. 4 is a diagram of the layers of the transfer pad of the present disclosure.

As shown in FIGS. 4-5, the body 11 of the transfer pad includes several sheets that perform important functions for the pad. The top sheet 20 is formed of a breathable non-woven material that allows moisture or fluid, such as sweat and urine, to pass through the sheet. The material of the top sheet 20 is very strong and rip-resistant since this sheet, together with the bottom sheet 24, will be subject to significant shear forces when a patient is being moved by the transfer pad 10. In one embodiment, the top sheet is formed of a non-woven polypropylene. The bottom sheet 24 can also be formed of the same breathable non-woven material, such as non-woven polypropylene. However, the bottom sheet is provided with a coating on its bottom surface that serves two purposes—to prevent passage of fluids and to reduce the friction of the bottom surface of the transfer pad. Thus, the bottom sheet is provided with a low-friction film 25 on its bottom surface that is also generally fluid-impermeable. The low-friction film allows the transfer pad 10 to slide easily on the surface of the bed or bed linens. This reduces the force needed by the caregivers to move the patient along the bed, thereby reducing the risk of musculoskeletal injury to the caregiver. In one embodiment, the film is a polyethylene film applied to the bottom surface of the bottom sheet 24. The low-friction film preferably has a static coefficient of friction of 0.33-0.45 and a kinetic coefficient of friction of 0.34-0.40. The static coefficient of friction is high enough that the patient cannot easily disengage the transfer pad 10 from the bed linens, but is low enough that the caregiver or nurse can start the transfer pad moving with the patient on it without exerting undue force. The force needed to start the pad moving on bed linens is under 0.20 lbf. Once the transfer pad has been disengaged from the bed linens, the force needed to overcome the kinetic coefficient of friction is also under 0.20 lbf. To put the coefficients of friction into context, for a 250 lb. patient, the force that must be overcome to slide the patient with the pad 10 is 100 lbf. This same polyethylene film is substantially fluid impermeable. In a specific embodiment, the polypropylene of the top and bottom sheets has a CAS Registry Number of 9003-07-0, while the polyethylene coating has a CAS Registry Number of 9002-88-4.

As shown in FIGS. 4-5, the top and bottom sheets 20, 24 have essentially the same configuration surface area. In a preferred embodiment, the thicknesses of the two sheets differ, with the bottom sheet being thicker to bear most of the load of moving the transfer pad with a patient resting thereon. In a specific embodiment, the top sheet 20 is polyethylene at a thickness of 0.004 inches (0.1 mm), with a weight of 23.04 grams for a 56"×30" pad. The corresponding bottom sheet 24 is polyethylene at a thickness of 0.014 inches (0.35 mm) and a weight of 245.95 grams.

The handles, whether the protruding handles 12 of FIGS. 1, 3 or the cut-outs 12' of FIGS. 2, 5, are incorporated into the sheets 20, 24. In a preferred embodiment, the cut-outs 12' are in the shape of a "dog bone" to improve the strength of the handles, as described in U.S. Pat. No. 8,281,436, owned by EHOB, Inc. (The "Detailed Description" of the '436 patent, and particularly col. 4, In. 7—col. 5, In. 23, is incorporated herein by reference.) In one embodiment that incorporates the protruding handles 12, the two sheets are connected around the inner perimeter 30 and the outer perimeter 31 of the two sheets in a conventional manner, such as by stitching or welding. In another embodiment incorporating the cut-out handles 12', the handles are defined in the top and bottom sheets, as shown in FIG. 5. In this embodiment, the sheets are stitched or welded together around the perimeter 32 of the cut-outs, as well as around the inner and outer perimeters 30, 31. It can be appreciated that in accordance with the present disclosure, the stitching or welding of the top and bottom sheets provides a leak-proof seam, at least at the inner perimeter 31.

Figures 6, 7:
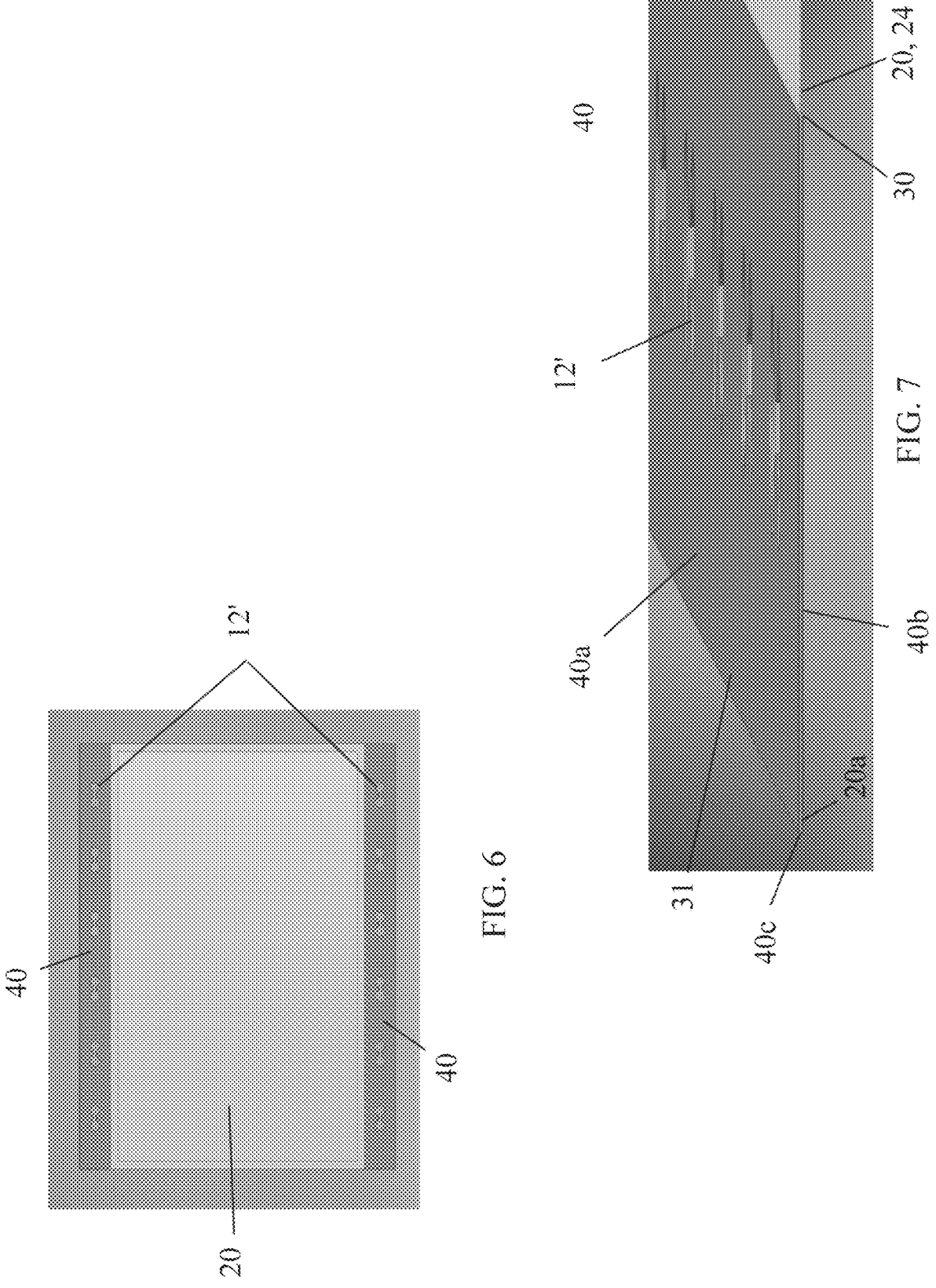
FIG. 6 is a top view of a transfer pad of the present disclosure with the handle portion shown in FIG. 2.
FIG. 7 is an enlarged partial view of the handle portion of the transfer pad shown in FIG. 6.

In a preferred embodiment, the "dog-bone" handles 12' are incorporated into a strip 40 that is affixed to the sides of the top and bottom sheets 20, 24, as shown in FIGS. 6-7. As best seen in FIG. 7, the strip 40 includes a top portion 40a that is positioned on the upper surface of the top sheet 20 and a bottom portion 40b that is positioned on the bottom surface of the bottom sheet 24. The strip 40 is a single sheet that is folded at fold 40c so that the top and bottom portions 40a, 40b overlap the top and bottom sheets 20, 24 and wrap around the side edge 20a of the sheets. The sheet 40, and particularly the portions 40a, 40b, are sized to extend from the inner perimeter 30 to the side edge 20a of the two sheets 20, 24. The cut-outs for the handles 12' are defined in the two strips and can overlap the two sheets. The inner perimeter 30 and outer perimeter 31 can be welded or sewn to affix the handle strips 40 to the top and bottom sheets, as shown in FIG. 2. In the preferred embodiment, the strips 40 are formed of the same non-woven polypropylene as the bottom sheet, with the same thickness (0.014 inches) in a specific embodiment. It can be appreciated that since the strips 40 are folded, the overall thickness of the handle portion of the pad is greater than the thickness of the absorbent core portion of the pad.

The transfer pad 10 includes an absorbent core configured to wick moisture away from the patient resting on the pad 10. In particular, the absorbent core includes a center sheet 22 that is bounded on its top and bottom sides by a tissue sheet 21, 23 that separates the center sheet from the top and bottom sheets 20, 24. The tissue sheets are formed of breathable or fluid-permeable material. In one embodiment, the tissue sheets are both formed of cellulose. It is contemplated that the bottom sheet 24 can also include a water-resistant coating, such as polyethylene, on the interior surface facing the center sheet, in addition to the polyethylene film on the bottom surface, to provide more assurance that fluid passing through the breathable top sheet 20 will be retained by the absorbent core. The center sheet 22 is formed of a cellulosic pulp and a super-absorbent polymer (SAP), such as sodium polyacrylate, which is adapted to absorb the bodily fluids that the pad 10 will encounter.

As shown in FIG. 4, the sheets of the absorbent core 21-23 have a smaller cross-section than the top and bottom sheets. Preferably, the core sheets 21-23 are sized to fit within the inner perimeter of the top and bottom sheets where the stitches or welds 30 are applied, to avoid compromising the material of the core sheets. Thus, the core is fully contained within the top and bottom sheets 21, 24 once those two sheets are sealed together. This prevents any leakage of fluids from the core outside the pad.

The transfer pad 10 is generally compliant to allow the caregivers to easily handle the pad when transferring a patient. However, the pad also has some stiffness, provided primarily by the polypropylene sheets, to prevent the pad from bunching when a patient moves while resting on the pad. For the more commonly-used pads, the pad can have a maximum thickness of less than 0.055 inches so that it does not take up much space in storage and so that it can be easily folded into a compact configuration for packaging. In particular, the thickness of the pad within the inner perimeter 30 is about 0.043 inches, based on the combined thickness of the top and bottom sheets 20, 24 and the three sheets 21-23 of the absorbent core. The thickness of the pad can be less at an inboard portion of the inner perimeter 30 where only the top and bottom sheets are welded or stitched together. The region with the handles 12' between the inner perimeter and outer perimeter 31 has a thickness of 0.051 inches, which includes the thickness of the top and bottom sheets 20, 24, as well as the overlapped portions 40a, 40b of the handle strip 40, and can include an outboard portion of the inner perimeter 30. While these dimensions are satisfactory for the more commonly-used pads based on the typical patient size, transfer pads for large patients can have a greater thickness in the region with the handles 12'. For "XL" sizes and above, the handle strip 40 can have a thickness of 0.020 inches, with the overall pad thickness increasing to about 0.070 inches.

The transfer pad 10 of the present disclosure is meant to aid caregivers and nurses in performing the essential functions of their job while reducing the risk of moving patients. The top absorbing portion of the pad absorbs any moisture that may be against the patient and locks it away so that the patient is not in danger of skin breakdown from their own fluids, and ensures that the patient is laying on a clean surface. The strong non-woven top and bottom sheets 20, 24 have a pull strength that ensures that the handles do not tear as the pad is pulled with the patient. More particularly, the construction of the top and bottom sheets and the construction of the cut-out handles 12' combine to provide significant pull strength. The construction of the pad 10 of the present disclosure requires a force of 98.5-138.5 lbf to tear the pad at a handle, according to testing under ASTM D882. It can be appreciated that if a single handle is used to move a 250 lb. patient, the friction force that must be overcome (100 lbf) would exceed the tear strength of the single handle. However, at a minimum, two handles would be used by a single caregiver on one side of the transfer pad, in which case the force to exceed the friction force to move the pad would be distributed between two handles, bringing the effective pull force in half, to 50 lbf, which is well within the strength range of each handle. If two caregivers pull from one side, four handles would be in use, which would reduce the pull force to ¼ at each handle.

Notwithstanding the pull strength of the handles, another critical feature of the transfer pad 10 is its ability to transfer a patient even when the pad has soaked up bodily fluids, such as urine from the patient. A soiled pad that tears when attempting to move a patient is essentially worthless. It can be appreciated that the pad must have sufficient tear strength when pulled in any direction. For testing purposes, the tear strength is evaluated for a pull force along the length and along the width of the pad. The soiled pad 10 of the present disclosure has a tear strength of 13-32 lbf in the length direction and of 11.5-20.5 lbf in the width direction of the pad, according to testing under NSTM D882. In this type of testing, a one-inch wide strip of the pad is subjected to a pull force. Thus, for a transfer pad that is 56 ins. long, the entire pad can withstand a much greater pull force without tearing. In more practical terms, the transfer pad 10 of the present disclosure can move a patient weighing over 400 lbs. using two handles.

The slick bottom surface of the bottom sheet 24 reduces friction to ease movement and the handles allow the caregiver to assume a more ergonomic position when moving the patient. Additionally, the handles provide a visual cue that distinguishes this transfer pad from other moisture absorbing pads that might be on the patient's bed and that lack any of the features of the transfer pad 10. In another feature, the handle strip 40 between the inner and outer perimeters 30, 31 can have a different color than the remainder of the pad 10. Thus, in a specific embodiment, the majority of the pad is white while the handle strip, which includes the handles 12', is green.

Figure 8:
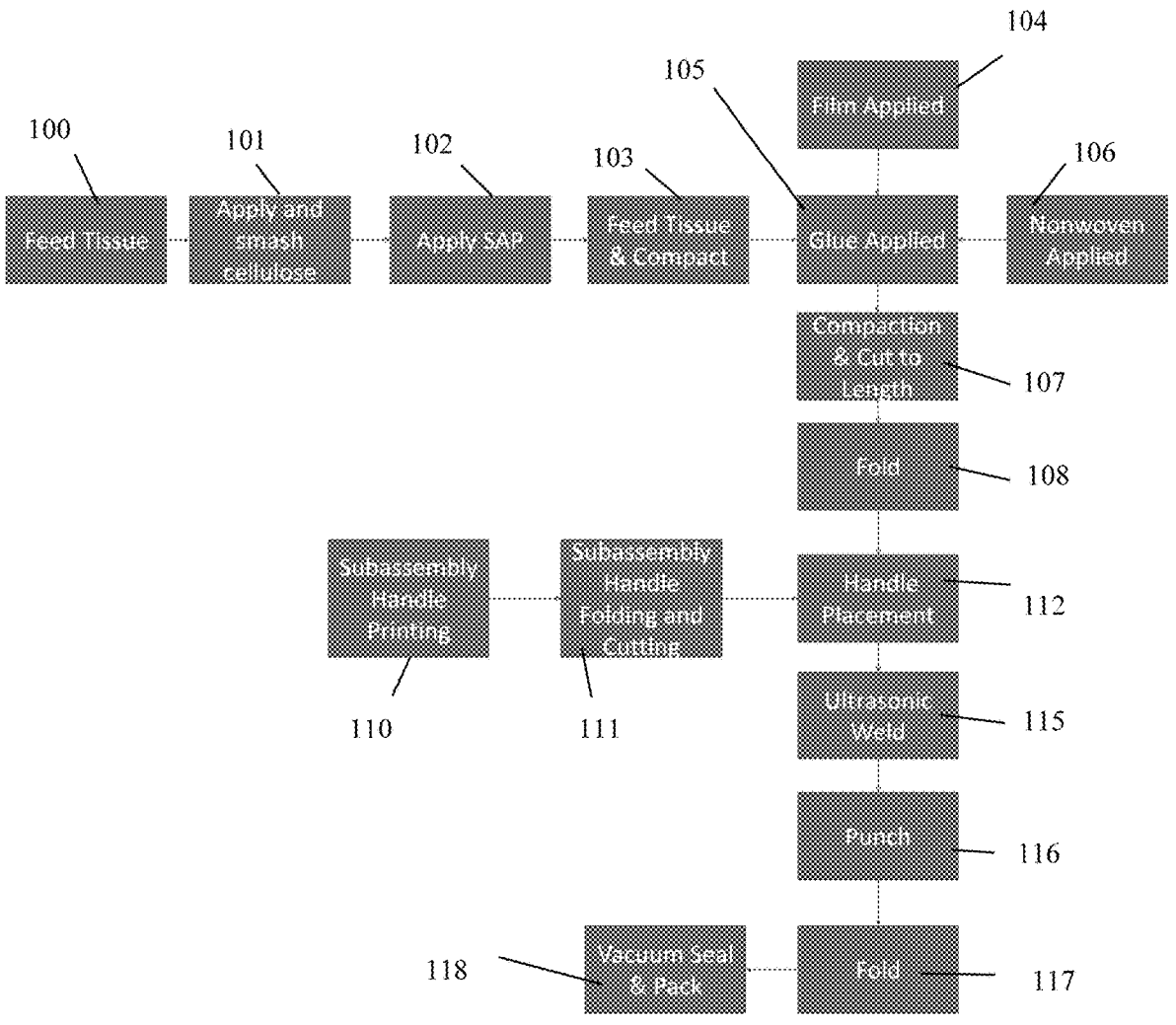
FIG. 8 is a flowchart of the steps in manufacturing the transfer pad of the present disclosure.

The pad 10 can be produced according to the steps in the flowchart of FIG. 8. A first sheet of tissue 23 is fed in Step 100. The cellulose is smashed or crushed and applied to the sheet of tissue in Step 101, after which the super-absorbent polymer is applied in Step 102. The second sheet of tissue 21 is overlaid on the cellulose and SAP and the three layers are compacted to a thickness of less than 0.040 inches in Step 103. The low-friction fluid-impermeable film, namely the polyethylene film, is applied in Step 104 to the exposed surface of the bottom sheet 24. An adhesive or glue is applied to the exposed surfaces of the two sheets of tissue 21, 23 in Step 105 and the top and bottom non-woven polypropylene sheets 20, 24 are applied to the exposed surfaces in Step 106. It can be appreciated that the glue and low-friction film can be allowed to set or cure before the next steps of the process are performed.

The completed layers 21-24 are compacted in Step 107 and cut to the desired length L. The sheets of tissue and non-woven polypropylene can be fed from continuous rolls with the travel paths of the sheets fed from the rolls overlapping. It can be appreciated that at this stage in the process, the top and bottom sheets 20, 24 are not yet sealed. To facilitate adding handles to the pad, the interim pad construction is folded in Step 108. The handles 12' are added in Steps 110-112. It is contemplated that at least two handles are provided on each side (width dimension) of the pad, with four handles spaced apart along each side being preferable to provide multiple gripping points for the caregiver or nurse. Thus, in Step 110, two handle strips 40 are prepared, with product and use information printed on the strips. In Step 111 the strips 40 are folded and cut to length. The handles are placed on the side edges of the interim pad construction in Step 112, with the portions 40a, 40b overlapping the top and bottom surfaces of the sheets 20, 24 and the fold 40c at the side edge 20a (FIG. 7). Once the handles strips 40 are positioned, the polypropylene sheets are ultrasonically welded together around the inner and outer perimeters 30, 31 and around the locations of the handles in Step 115. Alternatively, the welds can be replaced with a sewing operation. Once the sheets have been welded, the cut-outs for the handles 12' are punched from the welded sheets in Step 116.

The finished product is folded in Step 117 for vacuum sealed packaging in Step 118. It is contemplated that the transfer pad 10 of the present disclosure is disposable. The pads are folded into a compact package to minimize the storage requirement for keeping an adequate supply of pads 10. In addition, the pad can be folded in a manner that prominently displays the differently colored handle region described above within the packaging. This provides a clear visual cue to the caregiver of the absorbent transfer pad of the present disclosure, which improves efficiency. Efficiency is further improved by the manner in which the pad is folded. In particular, the pad is folded, as illustrated in FIG. 9, so that when the pad is unfolded next to a hospital bed the pad is immediately available to place under the patient. With the completed transfer pad 10 lying flat, the pad is folded over itself along the length of the pad. The handle strip is then folded back over the top half of the folded pad. The core or interior of the pad is folded under one handle strip and then repeated for the other handle strip so that the two handle strips overlay each other with only a small portion of the folded core or interior of the pad exposed to the side of the handle strips. The pad is then folded five times down the length of the pad, so that the 56 inch length is reduced to roughly 11 inches for packaging. When the pad is to be used, it is unfolded along the length with the folded pad as it appears in Step 6 of FIG. 9 placed along one side of the bed. The pad can be easily unfolded by pulling the exposed handle strip across the bed, unfurling the pad onto the bed.

The present disclosure should be considered as illustrative and not restrictive in character. It is understood that only certain embodiments have been presented and that all changes, modifications and further applications that come within the spirit of the disclosure are desired to be protected.

What is claimed is:

1. A transfer pad for use in transferring a person reclining with at least the person's torso and upper thighs on a bed with bed linens, comprising:

a top sheet formed from a fluid permeable material;

a bottom sheet having a bottom surface formed of a material having a coefficient of friction adapted to slide on the bed linens with the person on the transfer pad, wherein the top sheet and the bottom sheet are substantially identically sized to receive the torso and upper thighs of the person, and wherein the top sheet and bottom sheet are connected at a fluid leak-proof seam around a first perimeter of the top and bottom sheets;

an absorbent core disposed within the first perimeter between the top sheet and the bottom sheet, the absorbent core including in sequence;

a first tissue sheet;

a fluid absorbent sheet formed of a cellulosic pulp and a super-absorbent polymer (SAP); and a second tissue sheet;

handles defined along at least one side of the top and bottom sheets, the handles configured to be gripped by a person to move the transfer pad, wherein the top and bottom sheet define a second perimeter outside said first perimeter, and said handles are defined in said top and bottom sheets between said first perimeter and said second perimeter; and a strip affixed along the at least one side of the top and bottom sheets, said strip including said handles, wherein said strip is folded at the at least one side of the top and bottom sheets to include a top portion overlapping the top sheet and a bottom portion overlapping the bottom sheet, and said handles are defined continuously through the top portion of the strip, the top sheet, the bottom sheet and the bottom portion of the strip.

2. The transfer pad of claim 1, wherein the SAP is sodium polyacrylate.

3. The transfer pad of claim 1, wherein the first and second tissue sheets are formed of cellulose.

4. The transfer pad of claim 1, wherein said top sheet is formed of a breathable non-woven material.

5. The transfer pad of claim 4, wherein the breathable non-woven material is non-woven polypropylene.

6. The transfer pad of claim 1, wherein said bottom sheet is formed of a non-woven material.

7. The transfer pad of claim 6, wherein the non-woven material is non-woven polypropylene.

8. The transfer pad of claim 1, wherein said bottom surface formed of a material having a coefficient of friction adapted to slide of said bottom sheet is a coating applied to said bottom sheet.

9. The transfer pad of claim 8, wherein:

said bottom sheet is formed of non-woven polypropylene; and said coating is polyethylene.

10. The transfer pad of claim 9, wherein said polyethylene coating has a static coefficient of friction of 0.33-0.45 and a kinetic coefficient of friction of 0.34-0.40.

11. The transfer pad of claim 1, wherein said top sheet and said bottom sheet are formed of non-woven polypropylene, the bottom sheet having a thickness greater than said top sheet.

12. The transfer pad of claim 11, wherein said top sheet has a thickness of about 0.004 inches and said bottom sheet has a thickness of about 0.014 inches.

13. The transfer pad of claim 1, wherein the handles are dog-bone shaped.

14. The transfer pad of claim 1, wherein said strip is formed of non-woven polypropylene.

15. The transfer pad of claim 14, wherein:

said top and bottom sheets are formed of non-woven polypropylene; and said top sheet has a thickness of about 0.004 inches, said bottom sheet has a thickness of about 0.014 inches, and said strip has a thickness of 0.014-0.020 inches.

16. The transfer pad of claim 1, wherein the top sheet and the bottom sheet have a length of 39-72 inches and a width of 30-45 inches.

17. The transfer pad of claim 1, wherein said strip is affixed to said top and bottom sheets at said fluid leak-proof seam at said second perimeter.

* * * * *